United States Patent
Dogu et al.

(10) Patent No.: US 12,151,007 B2
(45) Date of Patent: Nov. 26, 2024

(54) ELECTROCHEMICAL TOOTH WHITENING COMPOSITION AND METHOD THEREOF

(71) Applicant: Colgate-Palmolive Company, New York, NY (US)

(72) Inventors: Nihal Dogu, Dayton, NJ (US); Leighton Davies-Smith, Lebanon, NJ (US)

(73) Assignee: Colgate-Palmolive Company, New York, NY (US)

( * ) Notice: Subject to any disclaimer, the term of this patent is extended or adjusted under 35 U.S.C. 154(b) by 350 days.

(21) Appl. No.: 16/912,904

(22) Filed: Jun. 26, 2020

(65) Prior Publication Data

US 2021/0401690 A1  Dec. 30, 2021

(51) Int. Cl.
| | |
|---|---|
| A61K 8/22 | (2006.01) |
| A61K 8/20 | (2006.01) |
| A61K 8/42 | (2006.01) |
| A61K 8/46 | (2006.01) |
| A61K 8/73 | (2006.01) |
| A61Q 11/00 | (2006.01) |

(52) U.S. Cl.
CPC .......... *A61K 8/22* (2013.01); *A61K 8/20* (2013.01); *A61K 8/42* (2013.01); *A61K 8/466* (2013.01); *A61K 8/731* (2013.01); *A61K 8/732* (2013.01); *A61K 8/737* (2013.01); *A61Q 11/00* (2013.01); *A61K 2800/30* (2013.01); *A61K 2800/48* (2013.01); *A61K 2800/83* (2013.01); *A61K 2800/88* (2013.01); *A61K 2800/92* (2013.01)

(58) Field of Classification Search
CPC ... A61K 8/22; A61K 8/20; A61K 8/42; A61K 8/466; A61K 8/731; A61K 8/732; A61K 8/737; A61K 2800/30; A61K 2800/48; A61K 2800/83; A61K 2800/88; A61K 2800/92; A61K 8/19; A61K 8/442; A61K 8/73; A61Q 11/00
See application file for complete search history.

(56) References Cited

U.S. PATENT DOCUMENTS

| | | |
|---|---|---|
| 7,775,795 B2 | 8/2010 | Khawaled et al. |
| 8,308,479 B2 | 11/2012 | Philp, Jr. et al. |
| 8,475,773 B2 | 7/2013 | Giles |
| 9,636,284 B2 | 5/2017 | Vierling et al. |
| 9,682,256 B2 | 6/2017 | Boyd et al. |
| 9,839,500 B2 | 12/2017 | Flyash |
| 2008/0003540 A1* | 1/2008 | Khawaled ............ A61K 8/38 433/32 |
| 2008/0050408 A1 | 2/2008 | Hayman et al. |
| 2008/0075676 A1 | 3/2008 | MacDonald et al. |
| 2011/0081628 A1 | 4/2011 | Alden, IV et al. |
| 2012/0213725 A1 | 8/2012 | Galleguillos et al. |
| 2012/0301522 A1* | 11/2012 | Prosise ............ A61Q 11/00 424/53 |
| 2014/0255867 A1* | 9/2014 | Kim ............ A61C 13/082 433/215 |
| 2016/0310379 A1* | 10/2016 | Khawaled ............ A61Q 11/02 |
| 2017/0367943 A1 | 12/2017 | Johansson et al. |
| 2018/0169057 A1 | 6/2018 | Abou-Chacra Vernet |
| 2018/0338890 A1 | 11/2018 | Glenn, Jr. et al. |

FOREIGN PATENT DOCUMENTS

| | | |
|---|---|---|
| AU | 2004222786 | 5/2005 |
| EP | 2504386 | 10/2012 |
| EP | 2883529 | 6/2015 |
| EP | 2934440 | 2/2018 |
| WO | 2008/001388 | 1/2008 |
| WO | 2014/098870 | 6/2014 |
| WO | 2016/051400 | 4/2016 |
| WO | 2018/118553 | 6/2018 |

OTHER PUBLICATIONS

International Search Report and the Written Opinion of the International Searching Authority issued in International Application PCT/US2021/038350 mailed Oct. 14, 2021, pp. 1-12.

* cited by examiner

Primary Examiner — Snigdha Maewall

(57) ABSTRACT

The present invention is directed to a process for electrochemically whitening a tooth, the process comprising: a) contacting the tooth with a whitening gel that is located in a dental device, the dental device comprising a positive electrode and a negative electrode; b) flowing a current between the positive electrode and the negative electrode through the whitening gel to whiten the tooth; wherein the whitening gel comprises: water; a bleaching agent; a thickener composition comprising a non-ionic compound; a surfactant; and an electrolyte source comprising a first conductive salt.

6 Claims, No Drawings

ELECTROCHEMICAL TOOTH WHITENING COMPOSITION AND METHOD THEREOF

BACKGROUND

Electrochemical tooth whitening processes include applying power to a conductive whitening gel, whereby the flowing electrical current through the conductive whitening gel activates a bleaching agent. Such activation accelerates the overall tooth whitening process. However, such previous electrochemical processes necessitate large amounts of an electrolyte source in the whitening gel to effectuate the necessary electrochemical response. Thus, a need exists for a new conductive whitening gel that overcomes such the limitations based on requiring large amounts of an electrolyte source in a conductive whitening gel.

BRIEF SUMMARY

The present invention includes a process for electrochemically whitening a tooth, the process comprising: a) contacting the tooth with a whitening gel that is located in a dental device, the dental device comprising a positive electrode and a negative electrode; b) flowing a current between the positive electrode and the negative electrode through whitening gel to whitening the tooth; wherein the whitening gel comprises: water; a bleaching agent; a thickener composition comprising a non-ionic compound; a surfactant; and an electrolyte source comprising a first conductive salt.

Other embodiments of the present invention include a process for electrochemically whitening a tooth, the process comprising: a) contacting the tooth with a whitening gel that is located in a dental device, the dental device comprising a positive electrode and a negative electrode; b) flowing a current between the positive electrode and the negative electrode through whitening gel to whitening the tooth; wherein the whitening gel comprises: water; a bleaching agent; a thickener composition comprising a non-ionic compound; and an electrolyte source comprising a first conductive salt; and wherein the whitening gel is substantially free of sulfate compounds.

Other embodiments of the present invention include a conductive tooth whitening gel comprising a single component blend of a bleaching agent; a thickener composition comprising a non-ionic compound; a surfactant; an electrolyte source comprising a first conductive salt; water in an amount ranging from about 65 wt. % to about 85 wt. % based on the total weight of the conductive tooth whitening gel; and a humectant in an amount ranging from about 1.0 wt. % to about 9.0 wt. % based on the total weight of the conductive tooth whitening gel.

Other embodiments of the present invention include a conductive tooth whitening gel comprising a single component blend of a bleaching agent; a thickener composition comprising a non-ionic compound; an electrolyte source comprising a first conductive salt; water in an amount ranging from about 65 wt. % to about 85 wt. % based on the total weight of the conductive tooth whitening gel; and a humectant in an amount ranging from about 1.0 wt. % to about 9.0 wt. % based on the total weight of the conductive tooth whitening gel; and wherein the whitening gel is substantially free of sulfate compounds.

Other embodiments of the present invention include a tooth-whitening kit comprising: a dental device comprising a trough having a positive electrode and a negative electrode; a whitening gel comprising: a bleaching agent; a thickener composition comprising a non-ionic compound; a surfactant; an electrolyte source comprising a first conductive salt.

Other embodiments of the present invention include a tooth-whitening kit comprising: a dental device comprising a trough having a positive electrode and a negative electrode; a whitening gel comprising: a bleaching agent; a thickener composition comprising a non-ionic compound; an electrolyte source comprising a first conductive salt; wherein the whitening gel is substantially free of sulfate compounds.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top," and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such.

Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

Unless otherwise specified, all percentages and amounts expressed herein and elsewhere in the specification should be understood to refer to percentages by weight. The amounts given are based on the active weight of the material. According to the present application, the term "about" means +/−5% of the reference value. According to the present application, the term "substantially free" less than about 0.1 wt. % based on the total of the referenced value.

The present invention is directed to a whitening gel, a kit comprising the whitening gel and a dental device, and a method of electrochemically whitening a tooth with the whitening gel and the dental device.

The whitening gel of the present invention may be conductive to be suitable for an electrochemical whitening process. The whitening gel may comprise a bleaching agent, a thickener composition, and an electrolyte source. The whitening gel of the present invention may further comprise a surfactant composition. The whitening gel of the present invention may further comprise a liquid carrier. The whitening gel of the present invention may further comprise a humectant.

The bleaching agent may comprise a peroxide source. Non-limiting examples of the peroxide source may include hydrogen peroxide, urea peroxide, glyceryl peroxide, benzoyl peroxide, and combinations thereof.

The bleaching agent may be present in an amount ranging from about 0.1 wt. % to about 18.0 wt. %—including all amounts and sub-ranges there-between—based on the total weight of the whitening gel. In some embodiments, the bleaching agent may be present in an amount ranging from about 1.0 wt. % to about 15.0 wt. %—including all amounts and sub-ranges there-between—based on the total weight of the whitening gel. In some embodiments, the bleaching agent may be present in an amount ranging from about 5.0 wt. % to about 11.0 wt. %—including all amounts and sub-ranges there-between—based on the total weight of the whitening gel. In some embodiments, the bleaching agent may be present in an amount of about 9.0 wt. %, based on the total weight of the whitening gel.

The whitening gel of the present invention may comprise a thickener composition. The thickener composition may impart rheological properties to the whitening gel. The thickener composition may also act to keep any solid phase of the whitening gel suspended, thus preventing separation of the solid phase portion of the oral care component from the liquid phase portion.

The thickener composition of the present invention may comprise a non-ionic compound or non-ionic component. The thickener composition of the present invention may consist essentially of the non-ionic compound or non-ionic component. The thickener composition of the present invention may consist of the non-ionic compound or non-ionic component. The thickener composition of the present invention may be substantially free of ionic compounds or ionic components. The thickener composition of the present invention may be substantially free of anionic compounds or anionic components. The thickener composition of the present invention may be substantially free of cationic compounds or cationic components.

The terms "ionic compounds" and "ionic components" refers to both low molecular weight ionic compounds (such as monomeric compounds as well as oligomeric compounds) as well as polymeric ionic components. The terms "anionic compounds" and "anionic components" refers to both low molecular weight anionic compounds (such as monomeric compounds as well as oligomeric compounds) as well as polymeric anionic components. The terms "cationic compounds" and "cationic components" refers to both low molecular weight cationic compounds (such as monomeric compounds as well as oligomeric compounds) as well as polymeric cationic components. In a non-limiting example, the thickener composition may be substantially free of anionic-charged polymer (such as anionic polyacrylic polymer).

Non-limiting examples of non-ionic compounds include cellulose ether, xanthan gum, carrageenan, carboxymethyl cellulose, hydroxyethyl cellulose, carboxymethyl hydroxyethyl cellulose, hydroxypropyl cellulose, ethyl hydroxyethyl cellulose, hydroxypropyl methylcellulose, guar gum, tragacanth gum, karaya gum, arabic gum, starch, and combinations thereof. In a preferred embodiment, the thickener composition is hydroxyethyl cellulose.

The thickener composition may be present in an amount ranging from about 0.1 wt. % to about 5.0 wt. %—including all amounts and subranges there-between—based on the total weight of the whitening gel. In some embodiments, the thickener composition may be present in an amount ranging from about 1.0 wt. % to about 4.0 wt. %—including all amounts and subranges there-between—based on the total weight of the whitening gel. In some embodiments, the thickener composition may be present in an amount ranging from about 2.0 wt. % to about 3.0 wt. %—including all amounts and subranges there-between—based on the total weight of the whitening gel. In some embodiments, the thickener composition may be present in an amount of about 2.5 wt. % based on the total weight of the whitening gel.

The whitening gel of the present invention may comprise a surfactant composition. The surfactant composition may comprise an amphoteric surfactant. Non-limiting examples of amphoteric surfactants include alkyl amine oxides, alkyl betaines, alkyl amidopropyl betaines, alkyl sulphobetaines (sultaines), alkyl glycinates, alkyl carboxyglycinates, alkyl amphoacetates, alkyl amphopropionates, alkylamphoglycinates, alkyl amidopropyl hydroxysultaines, acyl taurates and acyl glutamates, wherein the alkyl and acyl groups have from 8 to 19 carbon atoms.

In a non-limiting embodiment, suitable amphoteric surfactants include lauryl amine oxide, cocodimethyl sulphopropyl betaine, lauryl betaine, cocamidopropyl betaine, sodium cocoamphoacetate, and mixtures of two or more thereof. In a preferred embodiment, the amphoteric compound is cocamidopropyl betaine.

The surfactant composition may be present in an amount ranging from about 0.5 wt. % to about 6.0 wt. %—including all amounts and subranges there-between—based on the total weight of the whitening gel. In some embodiments, the surfactant composition may be present in an amount ranging from about 1.0 wt. % to about 5.0 wt. %—including all amounts and subranges there-between—based on the total weight of the whitening gel. In some embodiments, the surfactant composition may be present in an amount ranging from about 2.0 wt. % to about 4.0 wt. %—including all amounts and subranges there-between—based on the total weight of the whitening gel. In some embodiments, the surfactant composition may be present in an amount of about 3.0 wt. % based on the total weight of the whitening gel. In other embodiments, the whitening gel may be free of surfactant.

The surfactant composition may be substantially free of anionic surfactants and anionic compounds. The surfactant composition may be substantially free of cationic surfactants and cationic compounds. The surfactant composition may be substantially free of non-ionic surfactants. The surfactant composition may consist essentially for the amphoteric surfactant. The surfactant composition may consist of the amphoteric surfactant.

The surfactant composition may comprise the amphoteric surfactant in an amount ranging from about 90 wt. % to about 100 wt. %—including all amounts and subranges there-between—based on the total weight of the surfactant composition. In some embodiments, the surfactant composition may comprise the amphoteric surfactant in an amount ranging from about 95 wt. % to 100 wt. %—including all amounts and subranges there-between—based on the total weight of the surfactant composition. In some embodiments, the surfactant composition may comprise the amphoteric surfactant in an amount of about 100 wt. % based on the total weight of the surfactant composition.

The whitening gel of the present invention may be suitable for a electrochemical tooth whitening process. As such, the whitening gel of the present invention may exhibit a level of electric conductivity that allows electric current to flow through the whitening gel, thereby activate the bleaching agent and accelerating the overall tooth whitening process. To exhibit suitable electrical conductivity, the whitening gel of the present invention may comprise an electrolyte source capable of conduct ions.

The electrolyte source may comprise one or more conductive salts. Conductive salts may be selected from one or more of inorganic salts and organic salts. Non-limiting examples of conductive salts include chloride salts (such as sodium chloride, potassium chloride, lithium chloride, calcium chloride, strontium chloride, magnesium chloride or other chloride salts. Non-limiting of other salts include of sodium, potassium, lithium, calcium magnesium, strontium, fluoride, iodide, bromide. Non-limiting examples of potassium salts include water soluble potassium salt including potassium nitrate, potassium citrate, potassium chloride, potassium bicarbonate and potassium oxalate.

The electrolyte source may be present in an amount ranging from about 0.1 wt. % to about 8.0 wt. %—including all amounts and subranges there-between—based on the total weight of the whitening gel. The electrolyte source may be present in an amount ranging from about 0.5 wt. % to about 6.0 wt. %—including all amounts and subranges there-between—based on the total weight of the whitening gel. In some embodiments, the electrolyte source may be present in an amount ranging from about 1.0 wt. % to about 6.0 wt. %—including all amounts and subranges there-between—based on the total weight of the whitening gel.

In some embodiments, the electrolyte source may be present in an amount ranging from about 1.0 wt. % to about 3.0 wt. %—including all amounts and subranges there-between—based on the total weight of the whitening gel. In some embodiments, the electrolyte source may be present in an amount ranging from about 1.5 wt. % to about 2.5 wt. %—including all amounts and subranges there-between—based on the total weight of the whitening gel. In some embodiments, the electrolyte source may be present in an amount of about 2.0 wt. % based on the total weight of the whitening gel.

In other embodiments, the electrolyte source may be present in an amount ranging from about 5.0 wt. % to about 7.0 wt. %—including all amounts and subranges there-between—based on the total weight of the whitening gel. In other embodiments, the electrolyte source may be present in an amount ranging from about 5.5 wt. % to about 6.5 wt. %—including all amounts and subranges there-between—based on the total weight of the whitening gel. In other embodiments, the electrolyte source may be present in an amount of about 6.0 wt. % based on the total weight of the whitening gel.

The electrolyte source of the present invention may comprise a first conductive salt. In other embodiments, the electrolyte source may comprise a blend of a first conductive salt and a second conductive salt—whereby the first conductive salt is different from the second conductive salt.

Non-limiting examples of conductive salts include chloride salts (such as sodium chloride, potassium chloride, lithium chloride, calcium chloride, strontium chloride, magnesium chloride or other chloride salts), as well as salts of sodium, potassium, lithium, calcium magnesium, strontium, fluoride, iodide, bromide.

In some embodiments, the first conductive salt may be a sodium salt, a potassium salt, and combinations thereof. The sodium salt may be sodium chloride. The potassium salt may be selected from one of potassium chloride, potassium nitrate, and combinations thereof.

In some embodiments, the second conductive salt may be a sodium salt, a potassium salt, and combinations thereof. The sodium salt may be sodium chloride. The potassium salt may be selected from one of potassium chloride, potassium nitrate, and combinations thereof.

The second conductive salt and the first conductive salt are present in a weight ratio ranging from about 3:1 to about 1:3—including all ratios and sub-ranges there-between. In some embodiments, the second conductive salt and the first conductive salt are present in a weight ratio ranging from about 2:1 to about 1:2—including all ratios and sub-ranges there-between. In some embodiments, the second conductive salt and the first conductive salt are present in a weight ratio of about 1:1.

The first conductive salt may be present in an amount ranging from about 0.1 wt. % to about 2.0 wt. %—including all amounts and subranges there-between—based on the total weight of the whitening gel. In some embodiments, the first conductive salt may be present in an amount ranging from about 0.5 wt. % to about 1.5 wt. %—including all amounts and subranges there-between—based on the total weight of the whitening gel. In some embodiments, the first conductive salt may be present in an amount of about 1.0 wt. %, based on the total weight of the whitening gel.

The second conductive salt may be present in an amount ranging from about 0.1 wt. % to about 2.0 wt. %—including all amounts and subranges there-between—based on the total weight of the whitening gel. In some embodiments, the second conductive salt may be present in an amount ranging from about 0.5 wt. % to about 1.5 wt. %—including all amounts and subranges there-between—based on the total weight of the whitening gel. In some embodiments, the second conductive salt may be present in an amount of about 1.0 wt. %, based on the total weight of the whitening gel.

In some embodiments, the first conductive salt is sodium chloride and the second conductive salt is potassium chloride—whereby the second conductive salt and the first conductive salt are present in a weight ratio ranging from about 2:1 to about 1:2—including all ratios and sub-ranges there-between. In some embodiments, the first conductive salt is sodium chloride and the second conductive salt is potassium chloride—whereby the second conductive salt and the first conductive salt are present in a weight ratio of about 1:1.

In some embodiments, the first conductive salt is sodium chloride and the second conductive salt is potassium nitrate—whereby the second conductive salt and the first conductive salt are present in a weight ratio ranging from about 2:1 to about 1:2—including all ratios and sub-ranges there-between. In some embodiments, the first conductive salt is sodium chloride and the second conductive salt is potassium chloride—whereby the second conductive salt and the first conductive salt are present in a weight ratio of about 1:1.

The whitening gel of the present invention may further comprise a liquid carrier. Non-limiting examples of liquid carrier includes water. The water of the present invention may be deionized water, distilled water, or purified water.

The liquid carrier may be present in an amount ranging from about 65.0 wt. % to about 85.0 wt. %—including all amounts and subranges there-between—based on the total weight of the whitening gel. In some embodiments, the liquid carrier may be present in an amount ranging from about 70.0 wt. % to about 80.0 wt. %—including all amounts and subranges there-between—based on the total weight of the whitening gel. In some embodiments, the liquid carrier may be present in an amount of about 78.0 wt. %, based on the total weight of the whitening gel.

The whitening gel of the present invention may further comprise a humectant. Non-limiting examples of humectant include polyol compounds. Examples of humectants include glycerin, sorbitol propylene glycol, xylitol, lactitol, polypropylene glycol, polyethylene glycol, hydrogenated corn syrup, and mixtures thereof.

The humectant may be present in an amount ranging from about 1.0 wt. % to about 9.0 wt. %—including all amounts and subranges there-between—based on the total weight of the whitening gel. In some embodiments, the humectant may be present in an amount ranging from about 2.0 wt. % to about 8.0 wt. %—including all amounts and subranges there-between—based on the total weight of the whitening gel. In some embodiments, the humectant may be present in an amount ranging from about 3.0 wt. % to about 7.0 wt. %—including all amounts and subranges there-between—based on the total weight of the whitening gel. In some embodiments, the humectant may be present in an amount ranging from about 4.0 wt. % to about 6.0 wt. %—including all amounts and subranges there-between—based on the total weight of the whitening gel. In some embodiments, the humectant may be present in an amount of about 5.0 wt. % based on the total weight of the whitening gel.

The whitening gel of the present may further comprise one or more flavorant. Non-limiting examples of flavorant include wintergreen. The flavorant may be present in an amount ranging from about 0.1 wt. % to about 0.5 wt. %—including all amounts and subranges there-between—based on the total weight of the whitening gel. In some embodiments, the flavorant may be present in an amount of about 0.3 wt. % based on the total weight of the whitening gel.

The whitening gel of the present may further comprise one or more buffers. Non-limiting examples of buffers include primary, secondary, or tertiary alkali metal phosphates, citric acid, sodium citrate, sodium saccharin, tetrasodium pyrophosphate, sodium hydroxide, and combinations thereof. In a non-limiting example, the buffer may comprise sodium hydroxide and sodium saccharin in a 3:2 weight ratio.

The buffers may be present in an amount ranging from about 0.1 wt. % to about 1.5 wt. %—including all amounts and subranges there-between—based on the total weight of the whitening gel. In some embodiments, the buffers may be present in an amount of about 0.2 wt. % to about 1.1 wt. % based on the total weight of the whitening gel.

The whitening gel of the present invention may have a pH ranging from about 4.0 to about 6.5—including all pH values and subranges there-between. In some embodiments, the whitening gel of the present invention may have a pH ranging from about 5.0 to about 6.0—including all pH values and subranges there-between. In some embodiments, the whitening gel of the present invention may have a pH ranging from about 5.5 to about 5.8—including all pH values and subranges there-between.

The whitening gel of the present invention may have a viscosity that ranges from about 100,000 cP to about 900,000 cP—as measured by a V74 Spindle at 1 RPM—including all viscosities and subranges there-between. In some embodiments, the whitening gel of the present invention may have a viscosity that ranges from about 400,000 to about 750,000—as measured by a V74 Spindle at 1 RPM—including all viscosities and subranges there-between.

As discussed, the present invention includes an electrochemical tooth whitening process that includes flowing an electrical current through the conductive whitening gel, thereby activating the bleaching agent and accelerating the overall tooth whitening process. Based on the relationship between conductivity and whitening efficacy, it has been surprisingly discovered that the addition of the non-ionic compound of the thickener composition results in an unexpected improvement in whitening efficacy, even at low conductivity.

Specifically, it has been surprisingly discovered that the addition of the non-ionic compound of the thickener composition imparts a significant increase in mobility of ions through the whitening gel. Unlike non-ionic thicken agents, which have a net neutral charge, ionic thickening agents (specifically, anionic thickening agents) have a net negative charge. This negative charge present in the medium interferes with the mobility and current of the ions, preventing activation of the whitening gel. As a result, the overall amount of electrolyte source present in the whitening gel containing the non-ionic thickening composition may be decreased without sacrificing the requisite conductivity needed for the whitening gel to impart the desirable whitening efficacy.

It has also been surprisingly discovered that the addition of the amphoteric surfactant to the whitening gel helps build viscosity in the presence of conductive salts. Therefore, at the cathode, as the whitening gel is activated and gas is formed to generate foam, such formation helps the activated gel spread to the tooth.

The whitening gel of the present invention may have an electrical conductivity ranging from about 10.0 mS/cm to about 85.0 mS/cm—including all electrical conductivities and subranges there-between. In some embodiments, the whitening gel of the present invention may have an electrical conductivity ranging from about 55 mS/cm to about 85 mS/cm—including all electrical conductivities and subranges there-between. In some embodiments, the whitening gel of the present invention may have an electrical conductivity ranging from about 70 mS/cm to about 80 mS/cm—including all electrical conductivities and subranges there-between.

Additionally, the whitening gel formulation of the present invention may be formulated without change in pH value in comparison to whitening gels that utilize anionic thickening agents or thickening agents free of anionic or amphoteric thickening agents. As such, the newly discovered relationship between amphoteric thickening agent, electrolyte source, and conductivity provides an improved whitening gel and related method of electrochemical tooth whitening that can achieve desirable tooth whitening at requisite pH levels while requiring less electrolyte source, thereby imparting a cost savings.

The electrochemical process of the present invention includes first contacting a tooth with the whitening gel and applying a current to the whitening gel. In some embodiments, the whitening gel may be located in a dental device, whereby the dental device comprises a positive electrode and a negative electrode configured to apply the current to the whitening gel. The whitening gel may be in direct contact with both of the positive electrode and the negative electrode in the dental device.

The current applied to the whitening gel may be from a low-voltage DC power source—whereby the voltage ranges from about 1.0 VDC to about 6.0 VDC—including all voltages and subranges there-between. The current applied to the whitening gel may ranges from about 10.0 mA to about 40.0 mA—including all voltages and subranges there-between.

Another aspect of the present invention relates to the separation distance between the positive electrode and negative electrode. With the whitening gel of the present invention exhibiting an enhanced current, the distance separating the first electrode and the second electrode may be increased. The distance separating the positive electrode from the negative electrode may range from a non-zero value up to about 20 mm—including all values and subranges there-between. In some embodiments, the distance separating the positive electrode from the negative electrode may range from about 3 mm to about 20 mm—including all values and subranges there-between. In some embodiments, the distance separating the positive electrode from the negative electrode may range from about 5 mm to about 20 mm—including all values and subranges there-between. In some embodiments, the distance separating the positive electrode from the negative electrode may range from about 5 mm to about 17 mm—including all values and subranges there-between.

The present invention further comprises a kit that includes both the whitening gel and the dental device. The dental device may be a tray. The tray may comprise a trough. The positive electrode and the negative electrode may be at least partially located within the trough. The whitening gel may be located within the trough. According to the present invention, the whitening gel may be pre-applied to the dental device. In other embodiments, the whitening gel may be supplied in a separate container having a reservoir containing the whitening gel, whereby the user applied the whitening gel to the dental device at the time of tooth whitening. The kit may further comprise a power source electrically coupled to the positive electrode and the negative electrode. In other embodiments, the kit may be configured for the positive electrode and the negative electrode to be electrically connected to a power source. Non-limiting examples of a power source include a battery or an electrical socket. According to the embodiments where the dental device is configured to be electrically coupled to a wall socket, the dental device may further comprise an AC/DC power transformer.

Some embodiments of the present invention may include the following exemplary claim set.

Claim 1: A process for electrochemically whitening a tooth, the process comprising: a) contacting the tooth with a whitening gel and contacting the whitening gel with a positive electrode and a negative electrode of a dental device; b) flowing a current between the positive electrode and the negative electrode through the whitening gel to whiten the tooth; wherein the whitening gel comprises: water; a bleaching agent; a thickener composition comprising a non-ionic compound; and an electrolyte source comprising a first conductive salt; and wherein the whitening gel is substantially free of sulfate compounds.

Claim 2: The process according to claim 1, wherein the non-ionic compound is present in an amount ranging from about 1.0 wt. % to about 5.0 wt. % based on the total weight of the whitening gel.

Claim 3: The process according to any one of claims 1 to 2, wherein the non-ionic compound is selected from the group consisting of cellulose ether, xanthan gum, carrageenan, carboxymethyl cellulose, hydroxyethyl cellulose, carboxymethyl hydroxethyl cellulose, hydroxypropyl cellulose, ethyl hydroxyethyl cellulose, hydroxypropyl methylcellulose, guar gum, tragacanth gum, karaya gum, arabic gum, starch, and combinations thereof.

Claim 4: The process according to any one of claims 1 to 3, wherein the first conductive salt is selected from the group consisting of sodium chloride, potassium nitrate, and potassium chloride.

Claim 5: The process according to anyone of claims 1 to 4, wherein the electrolyte source comprises a second conductive salt is selected from the group consisting of sodium chloride, potassium nitrate, and potassium chloride, provided that the second conductive salt is different from the first conductive salt.

Claim 6: The process according to any one of claims 1 to 5, wherein the thickening agent is substantially free of anionic compounds.

Claim 7: The process according to any one of claims 1 to 6, wherein the bleaching agent comprises a peroxide source selected from the group consisting of hydrogen peroxide, urea peroxide, glyceryl peroxide, benzoyl peroxide.

Claim 8: The process according to any one of claims 1 to 7, wherein the whitening gel in step a) has a pH ranging from about 4.0 to about 6.5.

Claim 9: A conductive tooth whitening gel comprising a single component blend of a bleaching agent; a thickener composition comprising a non-ionic compound; an electrolyte source comprising a first conductive salt; water in an amount ranging from about 65 wt. % to about 85 wt. % based on the total weight of the conductive tooth whitening gel; and a humectant in an amount ranging from about 1.0 wt. % to about 9.0 wt. % based on the total weight of the conductive tooth whitening gel; and wherein the whitening gel is substantially free of sulfate compounds.

Claim 10: The conductive tooth whitening gel according to claim 9, wherein the non-ionic compound is present in an amount ranging from about 1.0 wt. % to about 5.0 wt. % based on the total weight of the conductive tooth whitening gel.

Claim 11: The conductive tooth whitening gel according to any one of claims 9 to 10, wherein the non-ionic compound is selected from the group consisting of cellulose ether, xanthan gum, carrageenan, carboxymethyl cellulose, hydroxyethyl cellulose, carboxymethyl hydroxethyl cellulose, hydroxypropyl cellulose, ethyl hydroxyethyl cellulose, hydroxypropyl methylcellulose, guar gum, tragacanth gum, karaya gum, arabic gum, starch, and combinations thereof.

Claim 12: The conductive tooth whitening gel according to any one of claims 9 to 11, wherein the first conductive salt is selected from the group consisting of sodium chloride, potassium nitrate, and potassium chloride.

Claim 13: The conductive tooth whitening gel according to anyone of claims 9 to 12, wherein the electrolyte source comprises a second conductive salt is selected from the group consisting of sodium chloride, potassium nitrate, and potassium chloride, provided that the second conductive salt is different from the first conductive salt.

Claim 14: The conductive tooth whitening gel according to any one of claims 9 to 13, wherein the thickening agent is substantially free of anionic compounds.

Claim 15: The conductive tooth whitening gel according to any one of claims 9 to 14, wherein the bleaching agent comprises a peroxide source selected from the group consisting of hydrogen peroxide, urea peroxide, glyceryl peroxide, benzoyl peroxide.

Claim 16: The conductive tooth whitening gel according to any one of claims 9 to 15, wherein the single component blend has a pH ranging from about 4.0 to about 6.5.

Claim 17: A tooth-whitening kit comprising: a dental device comprising a positive electrode and a negative electrode; a whitening gel comprising: a bleaching agent; a thickener composition comprising a non-ionic compound; an electrolyte source comprising a first conductive salt; wherein the whitening gel is substantially free of sulfate compounds.

Claim 18: The tooth-whitening kit according to claim 17, wherein the non-ionic compound is present in an amount ranging from about 1.0 wt. % to about 5.0 wt. % based on the total weight of the whitening gel.

Claim 19: The tooth-whitening kit according to any one of claims 17 to 18, wherein the non-ionic compound is selected from the group consisting of cellulose ether, xanthan gum, carrageenan, carboxymethyl cellulose, hydroxyethyl cellulose, carboxymethyl hydroxethyl cellulose, hydroxypropyl cellulose, ethyl hydroxyethyl cellulose, hydroxypropyl methylcellulose, guar gum, tragacanth gum, karaya gum, arabic gum, starch, and combinations thereof.

Claim 20: The tooth-whitening kit according to any one of claims 17 to 19, wherein the first conductive salt is selected from the group consisting of sodium chloride, potassium nitrate, and potassium chloride.

Claim 21: The tooth-whitening kit according to anyone of claims 17 to 20, wherein the electrolyte source comprises a second conductive salt selected from the group consisting of sodium chloride, potassium nitrate, and potassium chloride, provided that the second conductive salt is different from the first conductive salt.

Claim 22: The tooth-whitening kit according to any one of claims 17 to 21, wherein the thickening agent is substantially free of anionic compounds.

Claim 23: The tooth-whitening kit according to any one of claims 17 to 22, wherein the bleaching agent comprises a peroxide source selected from the group consisting of hydrogen peroxide, urea peroxide, glyceryl peroxide, benzoyl peroxide.

Claim 24: The tooth-whitening kit according to any one of claims 17 to 23, wherein the whitening gel further comprises water.

Claim 25: The tooth-whitening kit according to any one of claims 17 to 24, wherein the whitening gel has a pH ranging from about 4.0 to about 6.5.

Claim 26: The tooth-whitening kit according to any one of claims 17 to 25, wherein the dental device comprises a trough, the positive electrode and negative electrode located in the trough, and wherein the positive electrode and the negative electrode are spaced apart by a distance ranging from about 5 mm to about 20 mm.

Claim 27: The tooth-whitening kit according to any one of claims 17 to 26, wherein the first electrode and the second electrode are configured to be electrically connected to a power source.

Examples

An experiment was performed to test the unexpected improvement in conductivity of the whitening gel formulation of the present invention. Two formulations were prepared including a comparative formulation (Comparative Example 1—or "Comp. Ex. 1") and an inventive formulation (Example 1—or "Ex. 1"). The formulations included various components as set forth below
  Electrolyte Source: conductive salt
  Humectant: glycerin
  Surfactant: cocamidopropyl betaine
  Non-Ionic Thickener: hydroxyethyl cellulose
  Anionic Thickener: anionic polyacrylic gum
  Buffer: sodium hydroxide and sodium saccharin in a 3:2 weight ratio
  Flavorant: wintergreen flavor A conductivity test was then performed by applying equal amounts of current to each formulation and measuring the corresponding conductivity of each formulation. A whitening test was also conducted by applying equal amounts of each formulation on a tooth surface and subsequently performing a number of treatment cycles that included application of current to the whitening formulation, whereby enhanced whitening is represented by the amount of overall color change ($\Delta E$). The formulations and test results are set forth below in Table 1.

TABLE 1

|  | Comp. Ex. 1 | Comp. Ex. 2 | Comp. Ex. 3 | Ex. 1 | Ex. 2 |
|---|---|---|---|---|---|
| Water | 53.6 | 83.6 | 80.1 | 77.1 | 77.9 |
| Electrolyte Source | 3.0 | 3.0 | 7.0 | 6.0 | 2.0 |
| Humectant | 30.0 | — | — | 5.0 | 5.0 |
| Hydrogen Peroxide | 9.0 | 9.0 | 9.0 | 9.0 | 9.0 |
| Anionic Thickener | 3.0 | 3.0 | 3.0 | — | — |
| Non-Ionic Thickener | — | — | — | 2.5 | 2.5 |
| Surfactant | — | — | — | — | 3.0 |
| Buffer | 1.1 | 1.1 | 0.6 | 0.2 | 0.3 |
| Flavorant | 0.3 | 0.3 | 0.3 | 0.2 | 0.3 |
| Total | 100.0 | 100.0 | 100.0 | 100.0 | 100.0 |
| Whitening Treatment 1 ($\Delta E$) | — | -3.0 | — | — | -4.8 |
| Whitening Treatment 2 ($\Delta E$) | — | -5.2 | — | — | -8.9 |
| Whitening Treatment 3 ($\Delta E$) | — | -7.0 | — | — | -9.5 |
| Whitening Treatment 4 ($\Delta E$) | — | -8.6 | — | — | -14.1 |
| Whitening Treatment 5 ($\Delta E$) | — | -10.0 | — | — | -16.1 |
| pH | 5.3 | 5.3 | 5.5 | 5.7 | 5.6 |
| Conductivity (mS/cm) | 17.0 | 38.4 | 77.1 | 67.84 | 76.62 |
| Whitening Distance From Cathode (mm) | — | 0.6 | — | — | 12.7 |

The whitening gels of Comparative Examples 1-3 utilize an anionic thickener, while the whitening gels of Examples 1 and 2 utilizes a thickening composition comprising a non-ionic thickener (i.e., hydroxyethyl cellulose). All formulation of Examples 1-3 and Examples 1 and 2 exhibit a pH within the range of 5-6. Example 2 further includes an amphoteric surfactant while Comparative Examples 1-3 do not include the amphoteric surfactant.

As demonstrated by Table 1, the presence of the non-ionic thickener results in at least equivalent if not better conductivity and whitening performance than the anionic-counterparts. Specifically, Example 2 demonstrates a marked improvement in conductivity when utilizing both the non-ionic thickener and amphoteric surfactant when compared against the anionic thickener formulations. The formulation of Example 2 exhibited a conductivity greater than 76 mS/cm while containing only 2 wt. % of conductive salts compared against the whitening gels of Comparative Examples 1 and 2 that never exhibited a conductivity greater than 39 mS/cm even when containing 3.0 wt. % conductive salts. Only Comparative Example 3 exhibits a conductivity comparable to that of Example 1, however, Comparative Example 3 requires 7 wt. % conductive salt (i.e., 3.5× the amount of conductive salt in Example 1) to achieve such similar conductivity. Furthermore, the whitening performance of Example 2 reflects the unexpected improvement in conductivity when compared against that of Comparative Example 2.

Furthermore, looking to Examples 1 and 2—the non-ionic thickener allows for the addition of humectant without degradation to the resulting conductivity (and related whitening performance) when compared against Example 1, which contains humectant but exhibits inferior conductivity performance. The unexpected improvement in conductivity due to the non-ionic thickener—even in the presence of humectant—may be desirable or even necessary in whitening gel compositions due to storage stability concerns.

Finally, looking to Comparative Example 2 and Example 2, the whitening gel formulation of the present invention further provides an unexpected improvement in ion mobility throughout the whitening gel. Specifically, replacing the ionic thickener with the non-ionic thickener surprisingly allows for greater separation between the anode and cathode, while still achieving the necessary flow of current through the whitening gel. As a result, whitening devices may be designed with greater flexibility in placement of electrodes when used in combination with the whitening gel formulation of the present invention.

What is claimed is:

1. A tooth-whitening kit comprising:
   a dental device comprising a positive electrode and a negative electrode;
   a single component whitening gel comprising:
   a liquid carrier comprising water;
   a bleaching agent;
   a thickener composition present in an amount ranging from about 0.1 wt. % to about 5.0 wt. % based on the total weight of the single component whitening gel, the thickener comprising a non-ionic compound, the non-ionic compound comprising hydroxyethyl cellulose;
   a surfactant present in an amount ranging from about 0.5 wt. % to about 6.0 wt. % based on the total weight of the single component whitening gel, the surfactant comprising cocoamidopropyl betaine;
   a humectant present in an amount ranging from about 1.0 wt. % to about 9.0 wt. % based on the total weight of the single component whitening gel, the humectant comprising glycerin; and
   an electrolyte source comprising a conductive salt, wherein the conductive salt is selected from the group consisting of sodium chloride or potassium chloride.

2. The tooth-whitening kit according to claim 1, wherein the single component whitening gel is substantially free of sulfate compounds.

3. The tooth-whitening kit according to claim 1, wherein the thickening agent is substantially free of anionic compounds.

4. The tooth-whitening kit according to claim 1, wherein the bleaching agent comprises a peroxide source selected from the group consisting of hydrogen peroxide, urea peroxide, glyceryl peroxide, benzoyl peroxide.

5. The tooth-whitening kit according to claim 1, wherein the single component whitening gel has a pH ranging from about 4.0 to about 6.5.

6. The tooth-whitening kit according to claim 1, wherein the dental device comprises a trough, the positive electrode and negative electrode located in the trough, and wherein the positive electrode and the negative electrode are spaced apart by a distance ranging from about 5 mm to about 20 mm.

* * * * *